United States Patent
Montoya et al.

(10) Patent No.: US 10,588,848 B2
(45) Date of Patent: Mar. 17, 2020

(54) SKIN TIGHTENING COMPOSITIONS

(71) Applicant: L'OREAL, Paris (FR)

(72) Inventors: Mariana Montoya, Berkeley Heights, NJ (US); Angelike A. Galdi, Westfield, NJ (US); Susan Halpern Chirch, Basking Ridge, NJ (US); Hubert Tunchiao Lam, Berkeley Heights, NJ (US)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 15/728,530

(22) Filed: Oct. 10, 2017

(65) Prior Publication Data
US 2019/0105254 A1   Apr. 11, 2019

(51) Int. Cl.
| A61K 8/81 | (2006.01) |
| --- | --- |
| A61K 8/25 | (2006.01) |
| A61Q 19/08 | (2006.01) |
| A61K 8/02 | (2006.01) |
| A61K 8/73 | (2006.01) |
| A61K 8/37 | (2006.01) |
| A61K 8/34 | (2006.01) |
| A61K 8/19 | (2006.01) |
| A61K 8/26 | (2006.01) |

(52) U.S. Cl.
CPC ............ *A61K 8/8182* (2013.01); *A61K 8/022* (2013.01); *A61K 8/19* (2013.01); *A61K 8/25* (2013.01); *A61K 8/26* (2013.01); *A61K 8/345* (2013.01); *A61K 8/37* (2013.01); *A61K 8/73* (2013.01); *A61K 8/8152* (2013.01); *A61Q 19/08* (2013.01); *A61K 2800/43* (2013.01); *A61K 2800/48* (2013.01)

(58) Field of Classification Search
None
See application file for complete search history.

(56) References Cited

U.S. PATENT DOCUMENTS

| 4,664,910 A * | 5/1987 | Caserio ............... A61K 8/63 424/70.8 |
| --- | --- | --- |
| 4,965,071 A | 10/1990 | Kawan |
| 5,422,118 A * | 6/1995 | Brown ............... A61K 9/0014 424/449 |
| 6,060,547 A * | 5/2000 | Canter ............... A61K 8/06 424/401 |
| 6,139,826 A * | 10/2000 | Schraer ............... A61K 8/91 424/70.16 |
| 2003/0082221 A1 | 5/2003 | O'Halloran et al. |
| 2011/0300196 A1* | 12/2011 | Mohammadi ........ A45D 44/002 424/401 |
| 2013/0189332 A1 | 7/2013 | Breyfogle |
| 2013/0195783 A1* | 8/2013 | Breyfogle ............ A61K 8/25 424/62 |
| 2015/0016862 A1 | 1/2015 | Gordon et al. |
| 2015/0037380 A1 | 2/2015 | Newman et al. |
| 2015/0359714 A1 | 12/2015 | Rabe et al. |
| 2017/0189320 A1 | 7/2017 | Chiou et al. |

FOREIGN PATENT DOCUMENTS

| EP | 2221045 | * | 8/2010 |
| --- | --- | --- | --- |
| EP | 2404642 | | 1/2012 |
| EP | 3295928 A1 | | 3/2018 |
| WO | WO2013078550 | * | 6/2013 |

OTHER PUBLICATIONS

International Search Report and Written Opinion dated Jan. 4, 2019 in a PCT/US2018/052782.

* cited by examiner

*Primary Examiner* — Jennifer A Berrios
(74) *Attorney, Agent, or Firm* — Laetitia Leproust; Runzhi Zhao

(57) ABSTRACT

The present disclosure relates to cosmetic compositions that provide immediate skin-tightening and long-lasting improvements to the skin for the treatment of, for example, eye bags, facial wrinkles, and other age-related skin imperfections. The compositions comprise: (a) a first film former sodium silicate; (b) a second film former; (c) at least one polyvalent silicate; (d) at least one anionic associative polymeric thickener; (e) a third film former VP/VA Copolymer; (f) at least two plasticizer; (g) at least one treated or non treated iron oxide pigments; and (h) optionally at least one cosmetic powder.

17 Claims, No Drawings

SKIN TIGHTENING COMPOSITIONS

FIELD OF THE DISCLOSURE

The present disclosure relates to cosmetic compositions that provide immediate and long-lasting improvement to the skin. In particular, the compositions provide a physical tightening effect to the skin useful for treating eye bags, facial wrinkles, and other age-related skin imperfections.

BACKGROUND OF THE DISCLOSURE

Skin produces less collagen and elastin as it ages. For example, after the age of twenty, a person (human) produces about 1 percent less collagen in the skin each year. As a result, the skin becomes thinner and more fragile. Inevitably, wrinkles, crow's feet, age-spots, eye bags, and the like, begin to form.

Consumers often wish to improve the appearance of such age-related skin imperfections, preferably with instantaneous results. Many consumer products and procedures devoted to hiding and reducing wrinkles are available. Some products and procedures are simple and inexpensive, for example, applying make-up, particularly a primer or colored foundation, to cover the skin (and thereby cover and/or fill the wrinkles and provide a smoother look). Far more expensive and drastic procedures, such as surgical face lifts and Botox® injections, are also used to reduce the appearance of wrinkles. However, many consumers either cannot afford, or do not wish, to undergo such drastic cosmetic procedures. There are a number of lotions and creams which are formulated to hydrate the skin and make it more supple, thereby reducing the appearance of wrinkles. Some of these products contain active ingredients, for example, niacinamide, that help repair and rejuvenate skin over time. Unfortunately, however, all of these products and procedures have drawbacks.

Make-up products are often visible, offer minimal texture benefits, and have no long-term lasting effect on the skin. After removal of the make-up, the skin looks the same as before the make-up was applied. Common skin care products can have chronic, acute or both effects on the skin. Hydration and optical effects are common acute benefits, but these benefits quickly wear-off over time.

Attempts have been made to develop new categories of products to improve the appearance of skin without the drawbacks of existing products and procedures. One such family of products can be generally classified as "adhesive, contractile film formers". Film formers are chemical compositions that when applied to skin, leave a pliable, cohesive and continuous covering. A select group of film formers are also adhesive to the skin and contractile.

SUMMARY OF THE DISCLOSURE

The current disclosure relates to a skin tightening composition that imparts an instant sensation and physical skin tightening effect upon application to the skin, in particular, to eye bags and eye or facial wrinkles, without the drawbacks of other products. The present disclosure relates to a skin tightening film forming composition, which is typically an aqueous composition, comprising:
(a) from about 0.02% to about 10% by weight of a first film former sodium silicate;
(b) from about 0.01% to about 10% by weight of a second film former;
(c) from about 0.01% to about 1.0% by weight of at least one polyvalent silicate;
(d) from about 0.5% to about 20% by weight of at least one anionic associative polymeric thickener;
(e) from about 0.25% to about 10% by weight of a third film former selected from the group consisting of VP/VA Copolymer, PVM/VA Copolymer, polybutene, acrylates copolymer, galactoarabinan, polyssacharides;
(f) a first and a second plasticizer, wherein the first and the second plasticizer are selected from the group consisting of butyl stearate, butylene glycol, triethyl citrate, poloxamer, diisopropyl sebacate, acetyl tributyl citrate, glycerin, propanediol and the mixture thereof; and wherein the first and the second plasticizer are present in a ratio of about 1:3 to 3:1;
(g) from about 0.3% to about 3% by weight of at least one treated or non treated pigment; and
(h) optionally from about 0.1% to about 10% by weight of at least one cosmetic powder.

The composition typically provides an immediate tightening of the skin and reduces skin imperfections upon application to the skin.

In one or more embodiments, the first film former sodium silicate is present in an amount from about 2% to about 7% by weight of the total weight of the composition.

In some embodiments, the second film former is selected from the group consisting of colloidal silicas, pullulan, polycacrylate-21 (and) acrylates/dimethylaminoethylmethacrylate copolymer, polyurethanes, polysaccharides, polyvinylpyrrolidone, polyacrylates, acrylates copolymer, and mixtures thereof.

In one or embodiments, the second film former comprises a polysaccharide. In further embodiments, the polysaccharide is pullulan. In some embodiments, the polysaccharide contains one or more free hydroxyl groups.

In some embodiments, the second film former is present in an amount from 0.1% to 8% by weight of the total composition. In further embodiments, the at least one polyvalent silicate is selected from the group consisting of magnesium silicate, calcium silicate, aluminum silicate, a polyvalent silicate clay, montmorillonite, bentonite, smectite, and mixtures thereof. In further embodiments, the at least one polyvalent silicate thickener comprises montmorillonite.

In some embodiment, the polyvalent silicate is/are present in an amount of 0.3% to 0.8% by weight of the total composition.

In one or more embodiments, the at least one anionic associative polymeric thickener is selected from the group consisting of an acrylate copolymer, an acrylates/beheneth-25 methacrylate copolymer, an acrylates/steareth-20 methacrylate copolymer, and mixtures thereof. In some embodiment, the anionic associative polymeric thickener(s) is/are present in an amount from 1% to 10% by weight of the total composition.

In some embodiments, the third film former comprises VP/VA Copolymer. In one or more embodiments, the VP/VA Copolymer is present in an amount from about 2% to about 25% by weight of the total weight of the composition.

In some embodiments, the plasticizers are present in an amount from 5% to 13% by weight of the total composition.

In some embodiments, the composition comprises at least one cosmetic powder selected from the group consisting of talc, mica, magnesium carbonate, calcium carbonate, silica, titanium dioxide, zinc oxide, red iron oxide, yellow iron oxide, black iron oxide, polyethylene powder, methylmethacrylate powder, polymethyl methacrylate, nylon polystyrene powder, silk powder, crystalline cellulose, and mixtures thereof. In some embodiment, the at least one cosmetic powder comprises polymethyl methalcrylate.

Another aspect of the instant disclosure can include the following:
(a) from about 0.02% to about 10% by weight of a first film former sodium silicate;
(b) from about 0.01% to about 10% by weight of a second film former;
(c) from about 0.01% to about 1.0% by weight of montmorillonite;
(d) from about 0.5% to about 20% by weight of at least an acrylate copolymer;
(e) from about 0.25% to about 10% by weight of VP/VA Copolymer;
(f) a butyl stearate;
(g) propanediol;
(h) from about 0.3% to about 3% by weight of at least one treated or non treated pigment; and
(i) optionally from about 0.1% to about 10% by weight of at least one cosmetic powder;
wherein the butyl stearate and the propandiol are present in a ratio of about 1:3 to about 3:1;
wherein the composition provides a tightening sensation, and reduces skin imperfections upon application to the skin.

The instant disclosure also relates to methods for improving the appearance of skin comprising applying the compositions described herein to the skin. For example, the methods of improving the appearance of skin include methods for treating or reducing the appearance of wrinkles, blemishes, dryness, roughness, dullness, age spots, sagging, and/or puffy skin.

The instant disclosure also relates to methods for firming and/or tightening the skin comprising applying the compositions described herein to the skin and forming a skin-tightening film or layer on the skin.

DETAILED DESCRIPTION OF THE DISCLOSURE

The skin tightening aqueous film forming composition of the present disclosure, in the broadest sense, typically includes the following:
(a) from about 0.02% to about 10% by weight of a first film former sodium silicate;
(b) from about 0.01% to about 10% by weight of a second film former;
(c) from about 0.01% to about 1.0% by weight of at least one polyvalent silicate;
(d) from about 0.5% to about 20% by weight of at least one anionic associative polymeric thickener;
(e) from about 0.25% to about 10% by weight of a third film former selected from the group consisting of VP/VA Copolymer, PVM/VA Copolymer, polybutene, acrylates copolymer, galactoarabinan, polyssacharides;
(f) a first and a second plasticizer, wherein the first and the second plasticizer are selected from the group consisting of butyl stearate, butylene glycol, triethyl citrate, poloxamer, diisopropyl sebacate, acetyl tributyl citrate, glycerin, propanediol and the mixture thereof; and wherein the first and the second plasticizer are present in a ratio of about 1:3 to 3:1;
(g) from about 0.3% to about 3% by weight of at least one treated or non treated pigment; and
(h) optionally from about 0.1% to about 10% by weight of at least one cosmetic powder.

Upon application to the skin, the compositions provide an immediate tightening sensation and reduce skin imperfections.

In some embodiments, the film former sodium silicate is present in an amount from about 0.02%, 0.05%, 0.1%, 0.5%, 1%, 1.5%, 2%, 2.5%, 3%, 3.5%, 4%, 4.5%, 5% to about 5%, 5.5% 6%, 6.5%, 7%, 7.5%, 8%, 9% or 10% by weight of the total weight of the composition.

In some embodiments, a second film former may be selected, for example, from the group consisting of colloidal silica, pullulan, Polyacrylate-21 (and) acrylates/dimethylaminoethylmethacrylate copolymer, Polyurethanes, polysaccharides, polyvinylpyrrolidone, polyacrylates, acrylates copolymer, and mixtures thereof. In some cases, the second film former is a polysaccharide, which may have one or more free hydroxyl groups. Furthermore, in some cases, the polysaccharide is pullulan. Typically, the second film former is present in an amount from about 0.1%, 0.15%, 0.2%, 0.25%, 0.3%, 0.35%, 0.4%, 0.45%, 0.5%, 0.55%, 0.6%, 0.70%, 0.8%, 1%, 1.5%, 2%, 2.5%, 3.5%, 4%, 4.5%, 5%, 6% to about 6%, 6.5%, 7%, 7.5%, 8%, 8.5%, 9%, 9.5%, or 10% by weight of the total weight of composition.

In some embodiments, a third film former can be selected, for example, from the group consisting of Polyvinylpyrrolidone/Vinyl Acetate (VP/VA) Copolymer, PVM/VA Copolymer, polybutene, acrylates copolymer, galactoarabinan, polyssacharides. In some cases, the third film former is present in an amount from about 0.25%, 0.3%, 0.4%, 0.5%, 0.6%, 0.8%, 1%, 1.5%, 2%, 2.5%, 3%, 3.5%, 4%, 4.5%, 5% to about 4.5%, 5%, 5.5%, 6%, 6.5%, 7%, 8%, 9% or 10% by weight of the total weight of the composition.

The third film former improves the film integrity by decreasing the flaws, making the film more durable, influencing the dry time, the pigments distribution and the product texture.

Copolymers of vinylpyrrolidone and of vinyl acetate (INCI name: VP/VA copolymer) are commercially available from BASF under the tradename Luviskol® VA.

The polyvalent silicate may be selected from the group consisting of magnesium silicate, calcium silicate, aluminum silicate, a polyvalent silicate clay, montmorillonite, bentonite, smectite, and mixtures thereof. In some cases, the polyvalent silicate is a polyvalent silicate thickener, such as montmorillonite. In some cases, the polyvalent silicate is organically modified clay such as kaolinite, smectite, bentonite, and/or montmorillonite. The polyvalent silicate is typically present in an amount from about 0.01%, 0.1%, 0.3%, 0.4%, 0.5% to about 0.5%, 0.6%, 0.7%, 0.8%, or 0.9% by weight of the total weight of the composition.

The compositions of the disclosure typically include at least one anionic associative polymeric thickener. The at least one anionic associative polymeric thickener may be selected from the group consisting of an acrylate copolymer, an acrylates/beheneth-25 methacrylate copolymer, an acrylates/steareth-20 methacrylate copolymer, and mixtures thereof. Furthermore, the at least one anionic associative polymeric thickener may include acrylates/steareth-20 methacrylate copolymer such as Aculyn™ 22 (Dow Chemical Company); acrylates/beneneth-25 methacrylate copolymer such as Novethix™ (Lubrizol); acrylate copolymer such as Carbopol® Aqua SF-1 Polymer (Lubrizol). The at least one anionic associative polymer thickener is typically present in an amount from about 0.5%, 1%, 1.5%, 2%, 2.5%, 3%, 3.5%, 4%, 4.5%, 5%, 5.5%, 6%, 6.5%, 7%, 7.5%, 8%, 9%, 10% to about 10%, 10.5%, 11%, 11.5%, 12%, 12.5%, 13%, 13.5%, 14%, 14.5%, 15%, 15.5%, 16%, 16.5%, 17%, 17.5%, 18%, 19%, or 20% by weight of the total weight of the composition. Many anionic associative polymeric thickeners are water-soluble, and increase the viscosity of water or form an aqueous gel when the cosmetic compositions of the disclosure are dispersed/dissolved in water.

The compositions of the disclosure typically include two plasticizers. The two plasticizers may be, for example, butyl stearate, butylene glycol, triethyl citrate, poloxamer, diisopropyl sebacate, acetyl tributyl citrate, glycerin, propanediol, propylene glycol, polyethylene glycol, glycerol, sorbitol, dipropylene glycol, isohexadecane, and sodium hyaluronate. Typically, the plasticizers are present in a ratio of about 1:3 to 3:1; of about 1.5:2.5 to 2.5:1; to about 2:1.

The two plasticizers are typically present in the cosmetic composition in an amount from about 2%, 3%, 4%, 5%, 6%, 7%, 8%, 9%, 10%, 11%, 12%, 13%, to about 12%, 13% 14%, 15%, 16%, 17%, 18%, 19%, 20%, 21%, 22%, 23% 24% or 25% by weight of the total weight of the composition.

The compositions of the disclosure typically include at least one treated or non treated iron oxide pigments, titanium dioxide, ultramarine pigments or any organic pigments. In one or more embodiments, the at least one treated or non treated colorants or pigments may be chosen from pigments, dyes, such as liposoluble dyes, nacreous pigments, and pearling agents. Representative liposoluble dyes which may be used according to the present invention include Sudan Red, DC Red 17, DC Green 6, ß-carotene, soybean oil, Sudan Brown, DC Yellow 11, DC Violet 2, DC Orange 5, annatto, and quinoline yellow. The nacreous pigments which may be used according to the present invention may be chosen from white nacreous pigments such as mica coated with titanium or with bismuth oxychloride, colored nacreous pigments such as titanium mica with iron oxides, titanium mica with ferric blue or chromium oxide, titanium mica with an organic pigment chosen from those mentioned above, and nacreous pigments based on bismuth oxychloride.

The pigments, which may be used according to the current disclosure, may be chosen from white, colored, inorganic, organic, polymeric, nonpolymeric, treated and untreated pigments. Representative examples of mineral pigments include titanium dioxide, optionally surface-treated, zirconium oxide, zinc oxide, cerium oxide, iron oxides, chromium oxides, manganese violet, ultramarine blue, chromium hydrate, and ferric blue. Representative examples of organic pigments include carbon black, pigments of D & C type, and lakes based on cochineal carmine, barium, strontium, calcium, and aluminum.

The term "pigments" should be understood as meaning white or coloured particles or particles which afford a colour effect, which are insoluble in the medium of the composition, and which are intended to colour and/or opacify the composition and/or the deposit produced with the composition.

The pigments may thus be chosen from monochromatic mineral pigments, organic lakes, nacres, and pigments with an optical effect, for instance reflective pigments and goniochromatic pigments.

The at least one treated or untreated iron oxide pigments is typically present in an amount from about 0.3%, 0.4%, 0.5%, 0.6%, 0.8%, 1%, 1.1%, 1.2%, 1.3% to about 1.3%, 1.4%, 1.5%, 1.6%, 1.8%, 2%, 2.1%, 2.2%, 2.4%, 2.6%, 2.8% or 3% by weight of the total composition.

The compositions described herein may include at least one cosmetic powder. Cosmetic powders can be used to help formulate compositions that are smooth and soft on the skin. Representative cosmetic powders include, but are not limited to, talc, mica, magnesium carbonate, calcium carbonate, silica, titanium dioxide, zinc oxide, red iron oxide, yellow iron oxide, black iron oxide, polyethylene powder, methacrylate powder, polystyrene powder, silk powder, crystalline cellulose, starch, titanated mica, iron oxide titanated mica, bismuth oxychloride, and the like. Additional powders include, but are not limited to, inorganic powders, such as gums, chalk, Fuller's earth, kaolin, sericite, muscovite, phlogopite, synthetic mica, lepidolite, biotite, lithia mica, vermiculite, aluminum silicate, starch, smectite clays, alkyl and/or trialkyl aryl ammonium smectites, chemically modified magnesium aluminum silicate, organically modified montmorillonite clay, hydrated aluminum silicate, fumed aluminum starch octenyl succinate barium silicate, calcium silicate, magnesium silicate, strontium silicate, metal tungstate, magnesium, silica alumina, zeolite, barium sulfate, calcined calcium sulfate (calcined gypsum), calcium phosphate, fluorine apatite, hydroxyapatite, ceramic powder, metallic soap (zinc stearate, magnesium stearate, zinc myristate, calcium palmitate, and aluminum stearate), colloidal silicone dioxide, and boron nitride; organic powder, such as polyamide resin powder (nylon powder), cyclodextrin, methyl polymethacrylate powder, copolymer powder of styrene and acrylic acid, benzoguanamine resin powder, poly(ethylene tetrafluoride) powder, and carboxyvinyl polymer, cellulose powder, such as hydroxyethyl cellulose and sodium carboxymethyl cellulose, ethylene glycol monostearate; inorganic white pigments, such as magnesium oxide. Representative cosmetic powders include, for example, polymethylsilsesquioxane, methyl polymethacrylate crosspolymer, Nylon-12, silica and boron nitride, and combinations thereof.

In some cases, the cosmetic powder may be selected from the group consisting of talc, mica, magnesium carbonate, calcium carbonate, silica, titanium dioxide, zinc oxide, red iron oxide, yellow iron oxide, black iron oxide, polyethylene powder, methacrylate powder, polymethyl Methacrylate, polystyrene powder, silk powder, crystalline cellulose, and mixtures thereof. In some cases, the cosmetic powder is polymethyl methalcrylate.

When present, the one or more cosmetic powders may be present in an amount of 0.1% to about 25%, 0.1% to 20%, 0.1% to 15%, 0.1% to 10%, 0.1% to 8%, 0.1% to 6%, 0.1% to 4%, 0.5% to 20%, 0.0.5% to 15%, 0.5% to 10%, 0.5% to 8%, 0.5% to 6%, 0.5% to 4%, 1% to 20%, 1% to 15%, 1% to 10%, 1% to 8%, 1% to 6%, 1% to 4%, 2% to 10%, 2% to 8%, 2% to 6%, or 3% to 7%, based on the total weight of the composition.

The instant disclosure also relates to methods for improving the appearance of skin comprising applying the compositions described herein to the skin. Furthermore, the instant disclosure relates to methods for firming and/or tightening the skin comprising applying the compositions described herein to the skin and forming a skin-tightening film or layer on the skin. In some instances, the compositions are applied to the skin of the face, and/or more specifically around the eyes, around the mouth, and/or around the neck. The methods of improving the appearance of skin include methods for treating or reducing the appearance of wrinkles, blemishes, dryness, roughness, dullness, age spots, sagging, and/or puffy skin.

The compositions of the present disclosure may be in the form of a liquid dispersion, a gel, a cream, a lotion, a mousse, or a spray. The composition may be in the form of a liquid emulsion, such as a liquid-lotion, liquid-gel, liquid-cream, or a cream emulsion, such as a thick cream or gel-cream, foam or mousse wherein the liquid emulsion form has a thinner consistency than the cream emulsion form.

The compositions of the present disclosure are typically aqueous compositions. For example, the compositions may have 20% to 80%, 20% to 70%, 20% to 60%, 20% to 50%, 20% to 40%, 20% to 30%, 30% to 80%, 30% to 70%, 30% to 60%, 30% to 50%, 30% to 40%, 35% to 65%, or 40% to 60% water.

EXAMPLES

The following Examples are provided for illustrative purposes only, and are not intended to be limiting.

The following Table 1 shows inventive formula prepared according to the disclosure.

TABLE 1

| | Inventive Examples | | | | |
|---|---|---|---|---|---|
| Formula US INCI Name | Ex. 1 % | Ex. 2 % | Ex. 3 % | Ex. 4 % | Ex. 5 % |
| Dye/Pigment | 1.54 | 1.25 | 1.25 | 1.50 | 2 |
| Butyl Stearate | 10 | 10 | 8 | 10 | 10 |
| Sodium Silicate | 4.97 | 5.0 | 4.0 | 4.97 | 4.97 |
| Montmorillonite | 0.6 | 0.8 | 0.64 | 0.603 | 0.603 |
| Vp/Va Copolymer | 3 | 3.5 | 2.8 | 3 | 3 |
| Acrylates Copolymer | | | 15 | | |
| Acrylates Copolymer | 15 | 15 | 12 | 15 | 15 |
| Polyurethane-34 | | | 5 | | |
| Pullulan | 0.35 | 0.35 | 0.28 | 0.348 | 0.348 |
| Methyl Methacrylate Crosspolymer (And) Mineral Oil | 5 | 5 | 4 | 5 | 5 |
| Propanediol | 5 | 5 | 4 | 5 | 5 |
| Water | Q.S. | Q.S. | Q.S. | Q.S. | Q.S. |

In making the formulations in the above tables, the following procedure may be used. The polyvalent silicate, polysaccharide, and VP/VA Copolymer are introduced in portions with medium sweep and medium-high shear in main kettle at room temperature for about 10 minutes or until homogeneous. Next, the first plasticizer, butyl stearate is introduced followed by the pigments. The main kettle is then swept and homogenized well until the pigments are distributed evenly. Next, the remaining plasticizer is introduced followed by the cosmetic powder. The main kettle is swept and sheared for about 5-10 mins until homogenous. At this point, homogenizer is turned off and the vacuum is pulled to remove any aeration that may be present. Once the bubbles have been removed, the associative polymeric thickener is slowly added directly into the main kettle. Vacuum is then pulled again in the main kettle while sweeping to mix in the thickener. The sodium silicate is then slowly added to neutralize the thickener using low sweep while pulling vacuum. Continue to sweep until formula has thickened fully and is homogeneous and smooth.

The following Table 2 shows comparative formula prepared according to the disclosure.

TABLE 2

| | Comparative Examples | | | |
|---|---|---|---|---|
| Formula US INCI Name | Ex. 6 % | Ex. 7 % | Ex. 8 % | Ex. 9 % |
| Dye/Pigment | 1.71 | 0 | 0 | 0 |
| Butyl Stearate | 0 | 0 | 0 | 0 |
| Sodium Silicate | 4.97 | 4.97 | 5 | 5 |
| Montmorillonite | 0.603 | 0.603 | 1 | 0.5 |
| Vp/Va Copolymer | 0 | 0 | 0 | 0 |
| Acrylates Copolymer | 4.5 | 4.5 | 3 | 3 |
| Pullulan | 0.348 | 0.348 | 5 | 5 |
| Methyl Methacrylate Crosspolymer (And) Mineral Oil | 3 | 3 | 3 | 3 |
| Glycerin | 15 | 15 | 10 | 10 |
| Propanediol | 0 | 0 | 0 | 0 |
| Water | Q.S. | Q.S. | Q.S. | Q.S. |

Table 2 shows various compositions which were formed using the same process as Example 1.

The performances of the various compositions are shown in the following Table 3.

TABLE 3

| | Comparative Performances of Inventive and Comparative Examples | | | | | | |
|---|---|---|---|---|---|---|---|
| Formula Number | Ratio (Sodium Silicate:Montmorillonite) | Pullulan Levels | Film Plasticizers | Additional Film Formers | Blurring Powders | Tinted - % of pigment | Formula Performance |
| Ex. 1 | 8.24 | 0.35 | 10% Butyl Stearate 5% Propanediol | VP/VA Copolymer | 5 | Y - 1.54% (treated pigments) | +++ |
| Ex. 2 | 6.25 | 0.35 | 10% Butyl Stearate 5% Propanediol | VP/VA Copolymer | 5 | Y - 1.54% (treated pigments) | ++ (more flaws than Ex. 1) |
| Ex. 3 | 6.25 | 0.28 | 8% Butyl Stearate 4% Propanediol | VP/VA Copolymer, Polyurthane-34, Acrylates Copolymer | 4 | Y - 1.54% (treated pigments) | + (more significant flaws, unfavorable texture) |
| Ex. 4 | 8.2421 | 0.35 | 10% Butyl Stearate 5% Propanediol | VP/VA Copolymer | 5 | Y - 1.504% (untreated pigments) | +++ |
| Ex. 5 | 8.24 | 0.35 | 10% Butyl Stearate | VP/VA Copolymer | 5 | Y - 0.2% (treated | ++++ |

TABLE 3-continued

Comparative Performances of Inventive and Comparative Examples

| Formula Number | Ratio (Sodium Silicate:Montmorillonite) | Pullulan Levels | Film Plasticizers | Additional Film Formers | Blurring Powders | Tinted - % of pigment | Formula Performance |
|---|---|---|---|---|---|---|---|
| Ex. 6 | 8.24 | 0.35 | 5% Propanediol 15% Glycerin | — | 3 | Y - 1.504% (untreated pigments) | + (diminished effect, significant flaws) |
| Ex. 7 | 8.24 | 0.35 | 15% Glycerin | — | 3 | N | ++++ |
| Ex. 8 | 5 | 5 | 10% Glycerin | — | 3 | N | +(too tightening, significant flaws) |
| Ex. 9 | 10 | 5 | 10% Glycerin | — | 3 | N | ++ (significant flaws) |

(+) good formula -
(++) very good formula
(+++) excellent formula
(++++) best formula The present application was compared to formulas of Table 2. The compositions were applied on the face by an expert using fingers and compared to a bare face. The comparative examples of Table 2 provided a tightening sensation and visual changes to the skin within 5 minutes. Nonetheless, they presented many negative characteristics upon drying such as cracking of the film, flaking and incompatibility with various makeup regiments. The compositions of the instant disclosure showed significant improvements regarding the cracking and flaking. Furthermore, since the formulas contained pigments, the incompatibility with makeup was no more a concern.

In the section below, the tinted Formula 6 (Table 2) is compared with the untinted Formula 7. The objective of the study is to learn how the additional components in the tinted silicate formula (Formula 6) affected the efficacy when compared to the untinted formula (Formula 7).

To compare the two compositions, an expert evaluation on application, wear, flaws, irritation, was performed by an aesthetician using a 6 point scale atlas grading. The efficacy of both formula was examined at T=0, 10 min, 30 min, 3 hours, and 6 hours. Panelists with baseline Grade 4 eye bags experience a similar reduction of under eye bags and crow's feet. Flaws of cracking and flaking were rated low for both formulas. Overall, whether the formulas were tinted or untinted, the reduction followed similar trends, but having the tint that matches the skin tone is recommended.

Formulas from Table 2 demonstrated their ability to tighten the skin. The formulas though needed to be improved in order to minimize other flaws such as cracking, lifting, peeling and creasing as well as a long drying time. The challenge was to keep the benefit of the skin tightening while providing more comfort to the consumer while maintaining an efficacy to reduce the eye bags and the eye wrinkles. All the formula contained the same well known plasticizer, glycerin. The properties of the film were improved by replacing the glycerin with an optimal combination of butyl stearate and propanediol. The combination of the two plasticizers improved drastically the dry time and the texture. The formulas also showed that they were not compatible with the wear of make-up. The addition of a third film former was helpful to improve the strength of the film and its adhesion to the skin; especially in the case where pigments were present. It was observed by the consumers that the formula could be worn for over 8 hours.

In Table 3, we differentiated two types of formulas, the tinted formulas (Examples 1, 2, 3, 4, 5 and 6) and untinted formulas (Examples 7, 8 and 9) and reported their overall performances.

The ratio between the sodium silicate and the montmorillonite was studied and evaluated in order to show that it is one of the critical point in the present application as well as the level of pigments. Different formulas with different ratios were generated and evaluated. They are shown in Table 3. The best ratio between the sodium silicate and the montmorillonite was between a range of 6.2 and 8.4. The best level of pigment was observed between 0.2% and 1.54%.

In the case of the comparative Examples 6 and 7, the results showed that the performance was affected by the incorporation of pigments. Both film formulas tinted and untinted are at parity for reduction of under eye bags and crow's feet, however under eye wrinkles are less reduced at the 3 hour time point with Example 6. Flaws of cracking and flaking were rated low for both formulas. Example 6 demonstrated some dryness and creasing of lines under the eye. Overall, whether tinted or not tinted the reduction followed similar trends, but the incorporation of the pigments did affect the overall performance. According to the results in Table 3, the performance of the tinted formula (Example 6) was worse than the performance of the untinted formula (Example 7).

In the case of the inventive formulas (Examples 1, 2, 4 and 5), the performance were improved. The formulas demonstrated the best balance between flaws and efficacy. It is important to notice that the level of pigments impacts the overall performance. There is a balance between coverage and film integrity.

As used herein, all percentages are by weight (wt. %) of the total composition.

All numeric ranges are inclusive of narrower ranges; delineated upper and lower range limits are interchangeable to create further ranges not explicitly delineated. All ranges and values disclosed herein are inclusive and combinable. For examples, any value or point described herein that falls within a range described herein can serve as a minimum or maximum value to derive a sub-range, etc.

As used herein, the term "tightening" means that the film contracts in a manner that skin has a tighter sensation to the user, and smooths skin imperfections upon application on the skin, which reduces the visual appearance of wrinkles in the skin.

As used herein, the terms "comprising," "having," and "including" are used in their open, non-limiting sense.

The terms "a," "an," and "the" are understood to encompass the plural as well as the singular.

The expression "at least one" means "one or more" (and vice versa) and thus includes individual components as well as mixtures/combinations.

"Film former" or "film forming agent" as used herein means a polymer or resin that leaves a film on the substrate to which it is applied, for example, after a solvent accompanying the film former has evaporated, absorbed into and/or dissipated on the substrate.

All publications and patent applications cited in this specification are herein incorporated by reference, and for any and all purposes, as if each individual publication or patent application were specifically and individually indicated to be incorporated by reference. In the event of an inconsistency between the present disclosure and any publications or patent application incorporated herein by reference, the present disclosure controls.

The foregoing description illustrates and describes the disclosure. Additionally, the disclosure shows and describes only the exemplary embodiments but, as mentioned above, it is to be understood that it is capable to use in various other combinations, modifications, and environments and is capable of changes or modifications within the scope of the disclosed concepts as expressed herein, commensurate with the above teachings and/or the skill or knowledge of the relevant art. The embodiments described herein above are further intended to explain best modes known by applicant and to enable others skilled in the art to utilize the disclosure in such, or other, embodiments and with the various modifications required by the particular applications or uses thereof. Accordingly, the description is not intended to limit the invention to the form disclosed herein. Also, it is intended to the appended claims be construed to include alternative embodiments.

The invention claimed is:

1. A skin tightening aqueous film forming composition comprising:
    (a) from about 0.02% to about 10% by weight of a first film former sodium silicate;
    (b) from about 0.01% to about 10% by weight of a second film former;
    (c) from about 0.01% to about 1.0% by weight of at Montmorillonite;
    (d) from about 0.5% to about 20% by weight of at least an acrylate copolymer;
    (e) from about 0.25% to about 10% by weight of VP/VA Copolymer;
    (f) a first and a second plasticizer, wherein the first and the second plasticizer are butyl stearate and propanediol; and wherein the first and the second plasticizer are present in a ratio of about 2:1;
    (g) from about 0.3% to about 3% by weight of at least one treated or non treated pigment; and
    (h) optionally from about 0.1% to about 10% by weight of at least one cosmetic powder;
        wherein the composition provides a tightening sensation, and reduces skin imperfections upon application to the skin.

2. The composition of claim 1, wherein the first film former sodium silicate is present in an amount from about 2% to about 7% by weight of the total weight of the composition.

3. The composition of claim 1, wherein the second film former is selected from the group consisting of colloidal silica, pullulan, polycacrylate-21 (and) acrylates/dimethylaminoethylmethacrylate copolymer, polyurethanes, polysaccharides, polyvinylpyrrolidone, polyacrylates, acrylates copolymer, and mixtures thereof.

4. The composition of claim 3, wherein the second film former comprises a polysaccharide is pullulan.

5. The composition of claim 4, wherein the polysaccharide is pullulan.

6. The composition of claim 4, wherein the polysaccharide contains one or more free hydroxyl groups.

7. The composition of claim 1, wherein the second film former is present in an amount from 0.1% to 8% by weight of the total composition.

8. The composition of claim 1, wherein Montmorillonite is present in an amount of 0.3% to 0.8% by weight of the total composition.

9. The composition of claim 1, wherein the at least acrylate copolymer is present in an amount from 1% to 10% by weight of the total composition.

10. The composition of claim 1, wherein VP/VA Copolymer is present in an amount from about 1% to about 10% by weight of the total of the composition.

11. The composition of claim 1, wherein the plasticizers are present in an amount from 5% to 13% by weight of the total composition.

12. The composition of claim 1, wherein the composition comprises at least one cosmetic powder selected from the group consisting of talc, mica, magnesium carbonate, calcium carbonate, magnesium silicate, aluminum magnesium silicate, silica, titanium dioxide, zinc oxide, red iron oxide, yellow iron oxide, black iron oxide, polyethylene powder, methacrylate powder, polymethyl methacrylate, polystyrene powder, silk powder, crystalline cellulose, and mixtures thereof.

13. The composition of claim 12, wherein the at least one cosmetic powder comprises polymethyl methacrylate.

14. The composition of claim 1, wherein the pH of the composition is from about to about 12.

15. A method for improving the appearance of skin comprising applying the composition of claim 1 to the skin.

16. The methods of claim 15, wherein improving the appearance of skin comprises treating or reducing the appearance of wrinkles, blemishes, dryness, roughness, dullness, age spots, sagging, eye bags, and/or puffy skin.

17. A method for firming and/or tightening the skin comprising applying the composition of claim 1 to the skin.

* * * * *